United States Patent
Boulanger et al.

(10) Patent No.: US 11,702,103 B2
(45) Date of Patent: Jul. 18, 2023

(54) AFFECTIVE-COGNITIVE LOAD BASED DIGITAL ASSISTANT

(71) Applicant: HARMAN INTERNATIONAL INDUSTRIES, INCORPORATED, Stamford, CT (US)

(72) Inventors: Adam Boulanger, Palo Alto, CA (US); Sven Kratz, Saratoga, CA (US); Joseph Verbeke, San Francisco, CA (US); Priya Seshadri, Stamford, CT (US); Evgeny Burmistrov, Saratoga, CA (US); Neeka Mansourian, El Dorado Hills, CA (US); Stefan Marti, Oakland, CA (US)

(73) Assignee: Harman International Industries, Incorporated, Stamford, CT (US)

( * ) Notice: Subject to any disclaimer, the term of this patent is extended or adjusted under 35 U.S.C. 154(b) by 314 days.

(21) Appl. No.: 16/839,056

(22) Filed: Apr. 2, 2020

(65) Prior Publication Data

US 2021/0309252 A1 Oct. 7, 2021

(51) Int. Cl.
*B60W 60/00* (2020.01)
*B60W 40/08* (2012.01)
(Continued)

(52) U.S. Cl.
CPC ........ *B60W 60/0013* (2020.02); *B60W 40/08* (2013.01); *G06F 3/013* (2013.01); *G06F 3/015* (2013.01); *G06V 20/597* (2022.01); *B60W 2540/22* (2013.01); *B60W 2540/221* (2020.02); *B60W 2540/229* (2020.02); *G06F 2203/011* (2013.01)

(58) Field of Classification Search
CPC ............ B60W 60/0013; B60W 40/08; B60W 2540/22; B60W 2540/221; B60W 2540/229; G06F 3/013; G06F 3/015; G06F 2203/011; G06V 20/597
See application file for complete search history.

(56) References Cited

U.S. PATENT DOCUMENTS

| 10,399,575 | B2 * | 9/2019 | Spasojevic | ........ B60W 50/0098 |
| 2019/0197330 | A1 * | 6/2019 | Mahmoud | ............ G06N 3/0454 |

(Continued)

OTHER PUBLICATIONS

Zhu et al., "An ImprovedThree-Dimensional Model for Emotion Based on Fuzzy Theory", https://doi.org/10.4236/icc.2018.68008, 11 pages.

(Continued)

*Primary Examiner* — Aniss Chad
*Assistant Examiner* — Christine Nguyen Huynh
(74) *Attorney, Agent, or Firm* — Artegis Law Group, LLP

(57) ABSTRACT

Embodiments of the present disclosure sets forth a computer-implemented method comprising receiving, from at least one sensor, sensor data associated with an environment, computing, based on the sensor data, a cognitive load associated with a user within the environment, computing, based on the sensor data, an affective load associated with an emotional state of the user, determining, based on both the cognitive load at the affective load, an affective-cognitive load, determining, based on the affective-cognitive load, a user readiness state associated with the user, and causing one or more actions to occur based on the user readiness state.

19 Claims, 8 Drawing Sheets

(51) Int. Cl.
   *G06F 3/01*   (2006.01)
   *G06V 20/59*  (2022.01)

(56) References Cited

U.S. PATENT DOCUMENTS

2019/0239795 A1* 8/2019 Kotake ............... A61B 5/7267
2020/0031365 A1   1/2020 Marti et al.

OTHER PUBLICATIONS

Wikipedia, "PAD Emotional State Model", 3 pages https://en.wikipedia.org/w/index.php?title=PAD_emotional_state_model&oldid=919780281.
Le et al., "Investigation of spectral centroid features for cognitive load classification", doi:10.1016/j.pecom.2011.01.005 12 pages.
Zarjam et al., "Spectral EEG Features for Evaluating Cognitive Load", 33rd Annual International Conference of the IEEE EMBS, Boston, Massachusetts USA, Aug. 30-Sep. 3, 2011, 4 pages.
Wikipedia, "Emotion classification", Retrieved from the Internet:URL:https://en.wikipedia.org/w/index.php?title=Emotion classification&oldid=94 7269957, on Jan. 27, 2023, XP093018300, Mar. 25, 2020, pp. 1-16.

* cited by examiner

AFFECTIVE-COGNITIVE LOAD BASED DIGITAL ASSISTANT

BACKGROUND

Field of the Various Embodiments

The various embodiments relate generally to digital assistants and, more specifically, to an affective-cognitive load based digital assistant.

Description of the Related Art

Various digital systems include digital assistants that assist users to perform tasks. For example, various vehicles include an advanced driver assistance system (ADAS) that assists a driver in handling a vehicle. Such an ADAS may include a driver monitoring system (DMS) that monitors the driver in order to assess the driver's handling of the vehicle and enables the ADAS to respond to the state of the driver by providing various levels of assistance, such as by generating notifications, automating various driving tasks, etc.

A user typically splits focus between multiple objects when interacting with a given environment. For example, a driver may split focus between driving a vehicle and conducting a conversation with another person. In certain situations, the driver may not properly adjust to provide enough focus on driving tasks in order to adequately navigate complex driving situations that sporadically occur, such as an increase in traffic, adverse weather conditions, sudden obstacles, and so forth.

In general, an ADAS may easily detect distracting objects and may determine whether a driver is focused on the road. However, the driver monitoring system may not be able to determine the amount of focus the driver has when performing driving tasks. For example, the DMS may include a camera that is used to determine whether the driver's eyes are focused on the road, but the DMS may not account for other objects and stimuli that otherwise lessen the focus on successfully performing driving tasks. As a result, ADAS may not be able to effectively assist the driver and the driver may fail to modify their behavior to properly handle the necessary driving tasks.

In light of the above, more effective techniques for monitoring the status of the user interacting in an environment would be useful.

SUMMARY

One embodiment sets forth a computer-implemented method comprising receiving, from at least one sensor, sensor data associated with an environment, computing, based on the sensor data, a cognitive load associated with a user within the environment, computing, based on the sensor data, an affective load associated with an emotional state of the user, determining, based on both the cognitive load at the affective load, an affective-cognitive load, determining, based on the affective-cognitive load, a user readiness state associated with the user, and causing one or more actions to occur based on the user readiness state.

Further embodiments provide, among other things, a method and a system configured to implement the computer-readable storage medium set forth above.

At least one technological advantage of the disclosed techniques over previous digital assistant systems is that computing a user readiness state based on a combination of direct measurements that estimate the cognitive load of a user and the emotional state of the user provides a more accurate indication of the ability of the user to handle one or more tasks.

BRIEF DESCRIPTION OF THE DRAWINGS

So that the manner in which the above recited features of the various embodiments can be understood in detail, a more particular description of the inventive concepts, briefly summarized above, may be had by reference to various embodiments, some of which are illustrated in the appended drawings. It is to be noted, however, that the appended drawings illustrate only typical embodiments of the inventive concepts and are therefore not to be considered limiting of scope in any way, and that there are other equally effective embodiments.

DETAILED DESCRIPTION

In the following description, numerous specific details are set forth to provide a more thorough understanding of the various embodiments. However, it will be apparent to one of skilled in the art that the inventive concepts may be practiced without one or more of these specific details.

System Overview

Figure 1:
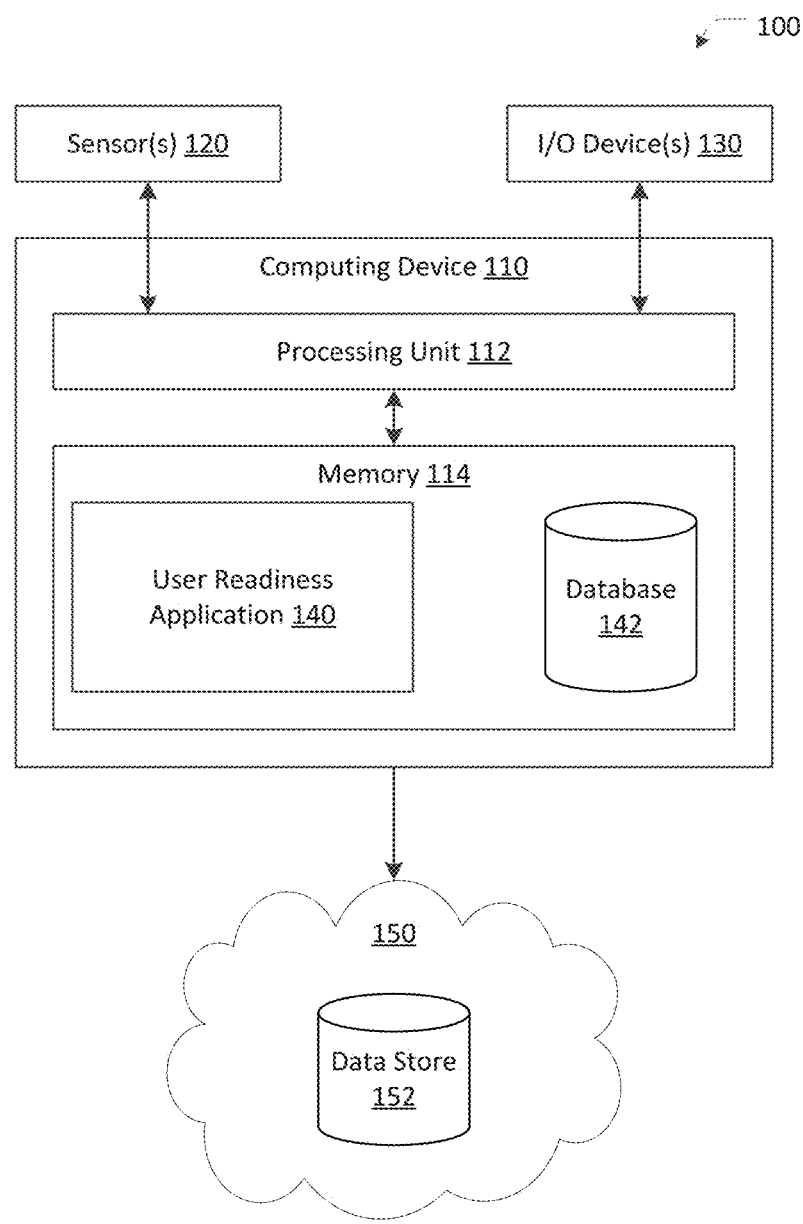
FIG. 1 illustrates a block diagram of the user readiness system configured to implement one or more aspects of the present disclosure.

FIG. 1 illustrates a block diagram of user readiness system 100 configured to implement one or more aspects of the present disclosure. As shown, user readiness system 100 includes, without limitation, computing device 110, sensor(s) 120, input/output (I/O) device(s) 130, and network 150. Computing device 110 includes processing unit 112 and memory 114, where memory 114 stores user readiness application 140 and database 142. Network 150 includes data store 152.

In operation, processing unit 112 receives sensor data from sensor(s) 120. Processing unit 112 executes user readiness system 140 to in order to process the sensor data and determine various biometric values associated with the psychophysiological state a user. Such biometric values include a cognitive load that estimates an amount of brain activity that a user is employing, and an affective load that estimates an emotion (specified as a pre-defined emotion or a set of emotion parameterized metrics associated with a psychophysiological state) that a user is experiencing. In various embodiments, the affective load may include one or more separate emotional metrics, such as separate arousal and/or valence values. Additionally or alternatively, the affective load may comprise one or more discrete emotional states and/or associated values of each. Upon determining biometric values for a user, user readiness application 140 combines the biometric values via one or more estimation algorithms to determine an affective-cognitive load (ACL) as a composite of the biometric values. In various embodiments, user readiness application 140 compares the ACL with other ACL data included in database 142 and/or data store 152 in order to map the ACL to a user readiness that estimates the ability of the user to handle one or more tasks. User readiness application 140 and/or other applications (not shown) may then generate output signals based on the determined user readiness state. For example, user readiness application 140 may be a component of an advanced driver assistance system (ADAS) that automates certain tasks and/or provides notifications via one or more output signals once user readiness application 140 determines that the user readiness is outside of a target value and/or target range.

As noted above, computing device 110 can include processing unit 112 and memory 114. Computing device 110 can be a device that includes one or more processing units 112, such as a system-on-a-chip (SoC). In various embodiments, computing device 110 may be a mobile computing device, such as a tablet computer, mobile phone, media player, and so forth. In some embodiments, computing device 110 may be a head unit included in a vehicle system. Generally, computing device 110 can be configured to coordinate the overall operation of user readiness system 100. The embodiments disclosed herein contemplate any technically-feasible system configured to implement the functionality of user readiness system 100 via computing device 110.

Various examples of computing device 110 include mobile devices (e.g., cellphones, tablets, laptops, etc.), wearable devices (e.g., watches, rings, bracelets, headphones, etc.), consumer products (e.g., gaming, gambling, etc.), smart home devices (e.g., smart lighting systems, security systems, digital assistants, etc.), communications systems (e.g., conference call systems, video conferencing systems, etc.), and so forth. Computing device 110 may be located in various environments including, without limitation, home environment (e.g., office, kitchen, etc.), road vehicle environments (e.g., consumer car, commercial truck, etc.), aerospace and/or aeronautical environments (e.g., airplanes, helicopters, spaceships, etc.), nautical and submarine environments, and so forth.

Processing unit 112 may include a central processing unit (CPU), a digital signal processing unit (DSP), a microprocessor, an application-specific integrated circuit (ASIC), a neural processing unit (NPU), a graphics processing unit (GPU), a field-programmable gate array (FPGA), and so forth. Processing unit 112 generally comprises a programmable processor that executes program instructions to manipulate input data. In some embodiments, processing unit 112 may include any number of processing cores, memories, and other modules for facilitating program execution. For example, processor unit 112 could receive input from a user via I/O devices 130 and generate pixels for display on I/O device 130 (e.g., a display device). In some embodiments, processing unit 112 can be configured to execute user readiness application 140 in order to analyze acquired sensor data and estimate the ability of a user to handle specific tasks by determining a user readiness state.

In such instances, user readiness application 140 may output the estimated user readiness state to one or more I/O modules 130 in order for the I/O modules 130 that respond to the determined user readiness state (e.g., output signals to provide assistance, output signals to enable a user to perform manual tasks, etc.).

Memory 114 can include a memory module or collection of memory modules. Memory 114 generally comprises storage chips such as random access memory (RAM) chips that store application programs and data for processing by processing unit 112. In various embodiments, memory 114 may include non-volatile memory, such as optical drives, magnetic drives, flash drives, or other storage. In some embodiments, separate data stores, such as data store 152 included in network 150 ("cloud storage") may supplement memory 114. User readiness application 140 within memory 114 can be executed by processing unit 112 to implement the overall functionality of the computing device 110 and, thus, to coordinate the operation of the user readiness system 100 as a whole.

User readiness application 140 processes acquire sensor data associated with a user and/or environment in order to determine various metrics associated with the user's brain activity and/or emotion. In various embodiments, user readiness application 140 may receive sensor data from one or more sensors 120 and may analyze the sensor data in order to determine the cognitive load of the user and/or the affective load, which may include separate emotional parameters that indicate the emotion being experienced by the user. User readiness application 140 determines, based on both the cognitive load and the affective load, an affective-cognitive load (ACL) of the user that indicates the user's overall mental activity and ability to manage a set of tasks. In various embodiments, user readiness application 140 may compare the ACL with other ACL values and/or thresholds in order to map the ACL to a specific user readiness state. User readiness application 140 may then output the user readiness state to one or more I/O devices 130 that respond to the determined user readiness state. For example, user readiness application 140 may determine that a current user readiness state is below the threshold level required to successfully navigate the current traffic conditions. User readiness application 140 could then send the user readiness state an ADAS that sends an output signal to I/O device 130 (e.g., a display device) in order to play a notification sound to alert the driver. In some instances, the ADAS could also respond by performing one or more automated tasks (e.g., assisted driving).

Database 142 can store values and other data retrieved by processing unit 112 to coordinate the operation of user readiness application 140. In various embodiments, processing unit 112 may be configured to store values in database 142 and/or retrieve values stored in database 142. For example, database 142 could store historical ACL values, lookup tables, ACL algorithms, mappings of sensor values to emotional parameterized metrics, mappings of ACL values to driver readiness levels, and so forth. In some embodiments, database 142 may store values retrieved from data store 152. In such instances, database 142 may receive periodic updates and provide values to user readiness application 140 between the periodic updates.

In various embodiments, database 142 can include one or more lookup tables, where the lookup tables store entries that include mappings between values. For example, database 142 could include a set of ACL lookup tables that includes entries of mappings of biometric values (e.g., cognitive load, affective load, arousal, valence, etc.), to ACL values. Additionally or alternatively, database 142 can include a set of ACL lookup tables that maps biometric values to pre-defined ACL levels (e.g., high ACL, medium ACL, low ACL, etc.), and/or a set of ACL lookup tables that maps pre-defined biometric values (e.g., a defined value for the psychophysiological trait of "angry") to specific ACL values and/or pre-defined ACL levels.

Sensor(s) 120 may include one or more devices that perform measurements and/or acquire data related to certain subjects in an environment. In various embodiments, sensor(s) 120 may generate sensor data that is related to the cognitive load and/or affective load of the user. For example, sensor(s) 120 could collect biometric data related to the user (e.g., heart rate, brain activity, skin conductance, blood oxygenation, pupil size, galvanic skin response, blood-pressure level, average blood glucose concentration, etc.). Additionally or alternatively, sensor(s) 120 can generate sensor data related to objects in the environment that are not the user. For example, sensor(s) 120 could generate sensor data about the operation of a vehicle, including the speed of the vehicle, pedal position, steering wheel position, ambient temperature in the vehicle, amount of light within the vehicle, and so forth. In some embodiments, sensor(s) 120 may be coupled to and/or included within computing device 110 and send sensor data to processing unit 112. Processing unit 112 executes user readiness application 140 in order to determine a user readiness state based on a determined cognitive-affective load that is derived from the acquired sensor data.

In various embodiments, sensor(s) 120 may acquire sensor data that user readiness application 140 processes in order to classify an emotion that the user is experiencing. For example, sensor(s) 120 could include a user-facing camera that records the face of the user as image data. User readiness application 140 could then analyze the image data in order to determine the facial expression of the user, and then map the facial expression to a specific emotion. In another example, sensor(s) 120 could include sensors in various parts of the vehicle (e.g., driver's seat passenger seat, steering wheel, etc.) that acquire biological and/or physiological signals of a user (e.g., perspiration, heart rate, heart-rate variability (HRV), blood flow, blood-oxygen levels, breathing rate, galvanic skin response (GSR), sounds created by a user, behaviors of a user, etc.). In such instances, user readiness application 140 could compute one or more quantitative emotional parameterized metrics, such as emotional arousal (A) and/or emotional valence (V) that indicate the emotion the user is experiencing.

In various embodiments, the sensor(s) 120 may also acquire data that user readiness application 140 processes in order to compute a cognitive load that a user is experiencing. For example, sensor(s) 120 could include a pupil sensor (e.g., a camera focused on the eyes of the user) that acquires image data about at least one pupil of the user. User readiness application 140 could then perform various pupillometry techniques to detect eye parameters (e.g., fluctuations in the user's pupil diameter, direction of the pupil is gazing, eye lid position, etc.) in order to estimate a cognitive load (CL) of the user. In another example, sensor(s) 120 could include heart rate sensors and/or other biometric sensors that acquire biological and/or physiological signals of the user (e.g., heart rate, breathing rate, eye motions, GSR, neural brain activity, etc.). In such instances, user readiness application 140 could compute the cognitive load from one or more of the acquired biological and/or physiological signals.

In various embodiments, the sensor(s) 120 may include optical sensors, such as RGB cameras, infrared cameras, depth cameras, and/or camera arrays, which include two or more of such cameras. Other optical sensors may include imagers and laser sensors. In some embodiments, sensor(s) 120 may include physical sensors, such as touch sensors, pressure sensors, position sensors (e.g., an accelerometer and/or an inertial measurement unit (IMU)), motion sensors, and so forth, that register the body position and/or movement of the user. In such instances, user readiness application 140 may analyze the acquired sensor data to determine the movement of the user, and then correlate such movement with specific emotions (e.g., boredom, fatigue, arousal, etc.) and/or a cognitive load of the user.

In various embodiments, the sensor(s) 120 may include physiology sensors, such as heart-rate monitors, electroencephalography (EEG) systems, radio sensors, thermal sensors, galvanic skin response sensors (e.g., sensors that measure change in electrical resistance of skin caused by emotional stress), contactless sensor systems, magnetoencephalography (MEG) systems, and so forth. In various embodiments, user readiness application 140 may execute spectral entropy, weighted mean frequency, bandwidth, and/or spectral edge frequency to determine cognitive load from the acquired sensor data.

In addition, in some embodiments, sensor(s) 120 may include acoustic sensors, such as a microphone and/or a microphone array that acquires sound data. Such sound data may be processed by user readiness application 140 performing various natural language (NL) processing techniques, sentiment analysis, and/or speech analysis in order to determine the semantic meaning of the phrases spoken in the environment and/or infer emotional parameterized metrics from the semantic meaning. In another example, user readiness application 140 could analyze the acquired sound data using voice-tone analysis in order to infer emotion from the speech signal included in the sound data. In some embodiments, user readiness application 140 may execute various analysis techniques relating to the spectral centroid frequency and/or amplitude of the sound signal in order to classify the sound signal to a specific value for the cognitive load.

In some embodiments, sensor(s) 120 may include behavioral sensors that detect the activity of the user within the environment. Such behavioral sensors may include devices that acquire related activity data, such as devices that acquire application usage data and/or mobile device usage data. In such instances, user readiness application 140 may estimate the cognitive load and/or the emotional parameterized metrics by determining the activities in which the user is currently engaged. For example, a given application could be classified as being a fun, social application in which a user engages when happy and active, and/or is making the user happy and active. In such instances, user readiness application 140 could correlate the usage of the given application with a pre-defined emotion (e.g., excited) and/or pre-defined emotional parameterized metrics (a high arousal value and a positive valence value).

I/O device(s) 130 may include devices capable of receiving input, such as a keyboard, a mouse, a touch-sensitive screen, a microphone and other input devices for providing input data to computing device 110. In various embodiments, I/O device(s) 130 may include devices capable of providing output, such as a display screen, loudspeakers, and the like. One or more of I/O devices 130 can be incorporated in computing device 110 or may be external to computing device 110. In some embodiments, computing device 110 and/or one or more I/O device(s) 130 may be components of an advanced driver assistance system. In various embodiments, user readiness application 140 may determine a cognitive load and/or an emotional load based on inputs received by one or more I/O devices 130. For example, the vehicle could include a head unit that includes a user interface. In such instances, user readiness application 140 could determine the cognitive load and/or the emotional load of the user based on one or more inputs received via the head unit.

Network 150 may enable communications between computing device 110 and other devices in network via wired and/or wireless communications protocols, satellite networks, V2X networks, including Bluetooth, Bluetooth low energy (BLE), wireless local area network (WiFi), cellular protocols, and/or near-field communications (NFC). In various embodiments, network 150 may include one or more data stores 152 that store data associated with sensor data, biometric values, affective-cognitive loads, and/or driver readiness levels. In various embodiments, user readiness application 140 and/or other digital assistants included in other devices may retrieve information from the data store 152. In such instances, user readiness application 140 may analyze the retrieved data as part of determining the ACL of the user, comparing the ACL to situations that involve specific ACL values, and so forth.

Figure 2:
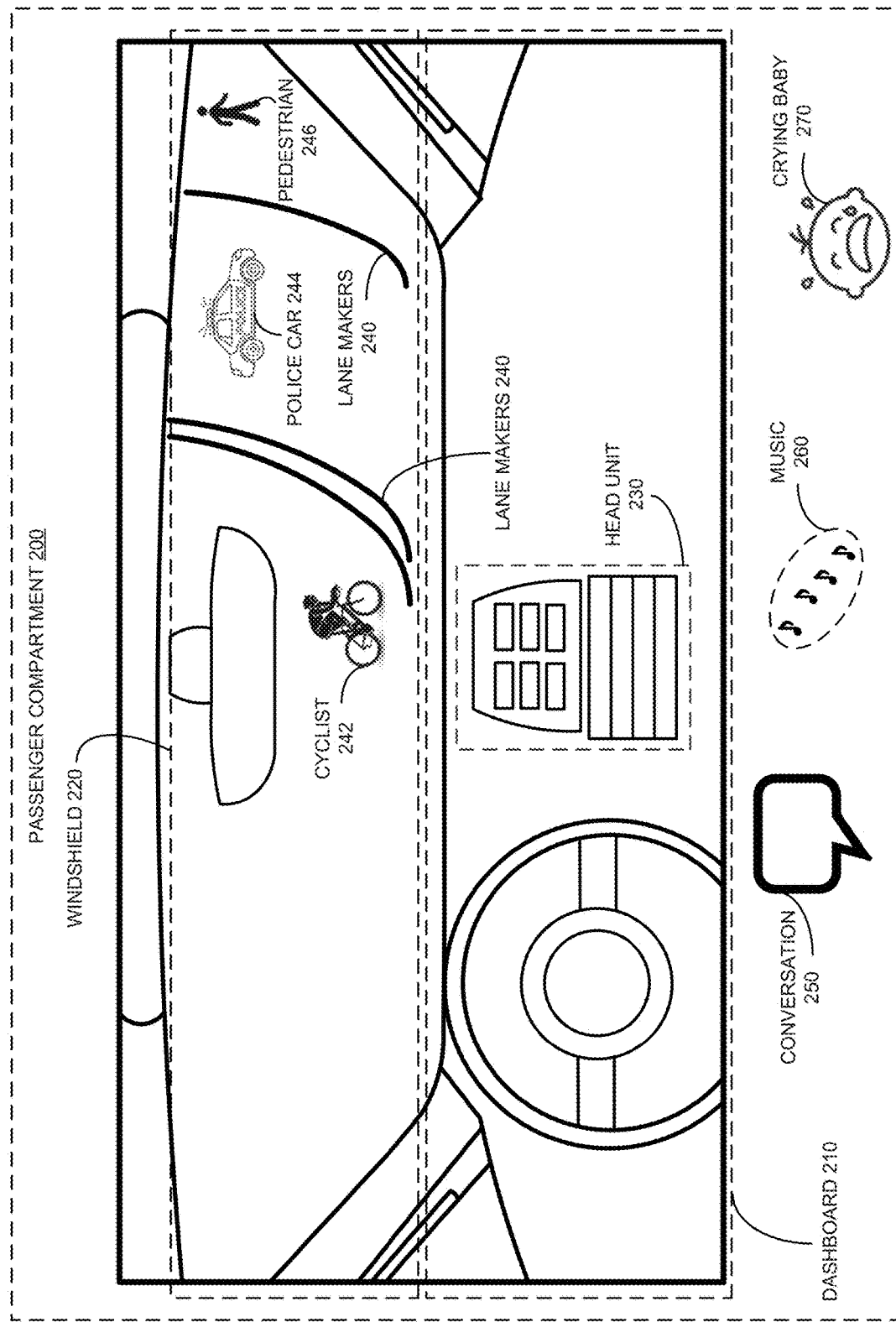
FIG. 2 illustrates a passenger compartment of a vehicle that is configured to implement the user readiness system of FIG. 1, according to various embodiments.

FIG. 2 illustrates a passenger compartment 200 of a vehicle that is configured to implement the user readiness system 100 of FIG. 1, according to various embodiments. As shown, passenger compartment 200 includes, without limitation, dashboard 210, windshield 220, and head unit 230. In various embodiments, passenger compartment 200 may include any number of additional components that implement any technically-feasible functionality. For example, passenger compartment 200 could include a rear-view camera (not shown).

As shown, head unit 230 is located in the center of dashboard 210. In various embodiments, head unit 230 may be mounted at any location within passenger compartment 200 in any technically-feasible fashion that does not block the windshield 220. Head unit 230 may include any number and type of instrumentation and applications and may provide any number of input and output mechanisms. For example, head unit 230 could enable users (e.g., the driver and/or passengers) to control entertainment functionality. In some embodiments, head unit 230 may include navigation functionality and/or advanced driver assistance (ADA) functionality designed to increase driver safety, automate driving tasks, and so forth.

Head unit 230 supports any number of input and output data types and formats, as known in the art. For example, head unit 230 could include built-in Bluetooth for hands-free calling and/or audio streaming, universal serial bus (USB) connections, speech recognition, rear-view camera inputs, video outputs for any number and type of displays, and any number of audio outputs. In general, any number of sensors (e.g., sensor(s) 120), displays, receivers, transmitters, etc., may be integrated into head unit 230, or may be implemented externally to head unit 230. In various embodiments, external devices may communicate with head unit 230 in any technically-feasible fashion.

While driving, the driver of the vehicle is exposed to a variety of stimuli that are related to either a primary task (e.g., guiding the vehicle) and/or any number of secondary tasks. For example, the driver could see via windshield 220, lane markers 240, cyclist 242, a specialized car 244, and/or pedestrian 246. In response, the driver could steer the vehicle to track lane markers 240 while avoiding cyclist 242 and pedestrian 246, and then apply the brake pedal to allow police car 244 to cross the road in front of the vehicle. Further, the driver could concurrently or intermittently participate in conversation 250, listen to music 260, and/or attempt to soothe crying baby 270.

As shown, differing driving environments and/or engagement in secondary activities (e.g., deep thinking, emotional conversations, etc.) typically increase the cognitive load experienced by the driver and may contribute to an unsafe driving environment for the driver and for in the proximity of the vehicle. In addition, the emotion experienced by the driver may also contribute to the unsafe driving environment, as the emotion that the user is experiencing may increase or decrease the ability of the driver to handle driving tasks.

The Affective-Cognitive Load Based Digital Assistant

Figure 3:
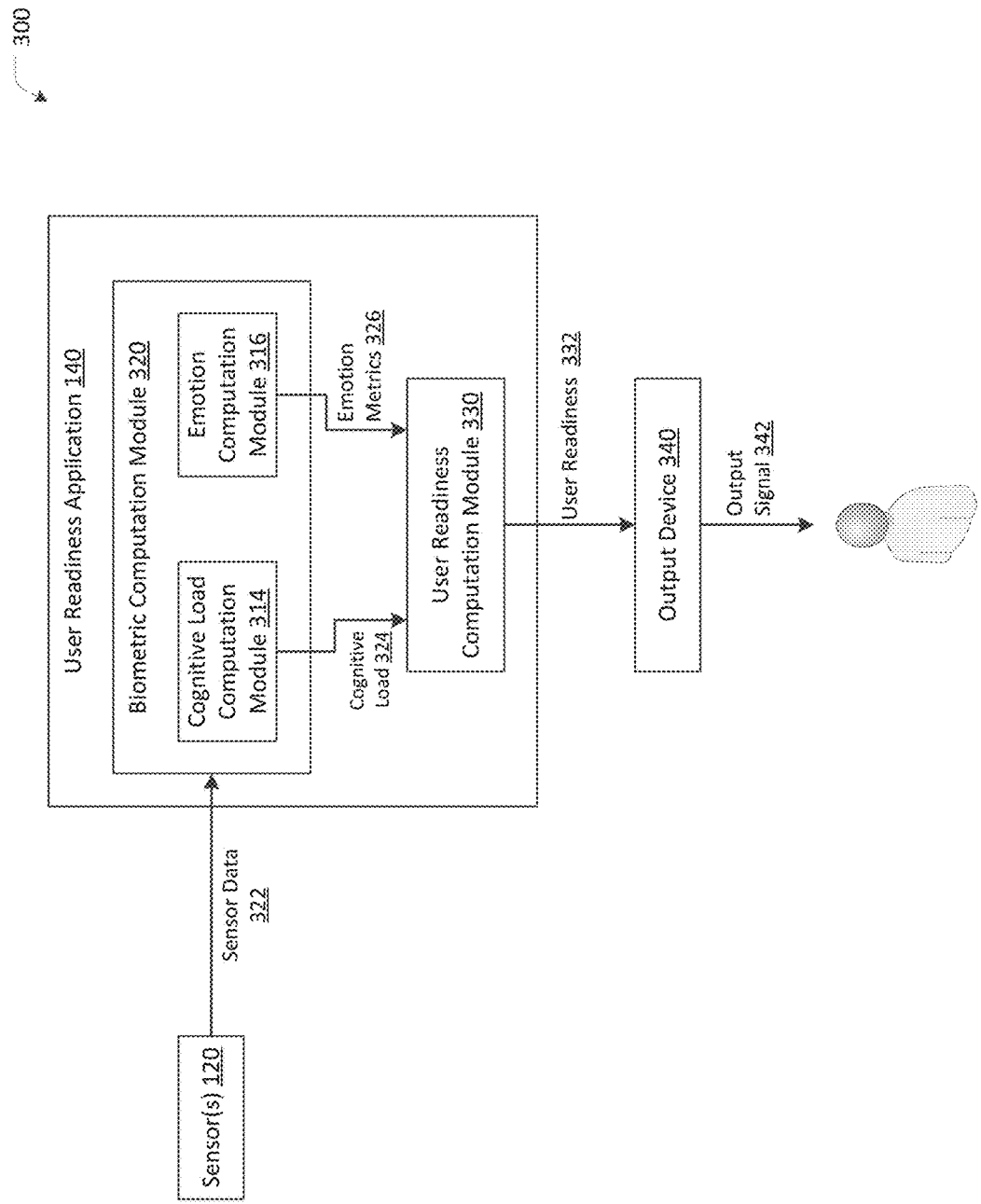
FIG. 3 illustrates a block diagram of the user readiness application of FIG. 1, according to various embodiments.

FIG. 3 illustrate affective-cognitive load-based assistant 300 included in the user readiness system 100 of FIG. 1, according to various embodiments. As shown, affective-cognitive load-based assistant 300 includes sensor(s) 120, user readiness application 140, and output device 340. User readiness application 140 includes biometric computation module 320 (including cognitive load computation module 314 and emotion computation module 316) and user readiness computation module 330.

In operation, biometric computation module 320 includes various modules 314, 316 that analyze sensor data 322 received from sensor(s) 120 in order to determine one or more biometric values, including cognitive load 324 and/or emotion metrics 326. Biometric computation module 320 sends biometric values 324, 326 to user readiness computation module 330 that performs one or more algorithmic techniques in order to determine an affective-cognitive load (ACL) of the user. User readiness computation module 330 may then map the ACL onto user readiness state 332 that indicates the ability of the user to handle tasks. User readiness computation module 330 sends the user readiness state 332 to one or more output device(s) 340 that provide output signal(s) 342 that affect the user and/or modify the behavior of the vehicle. For example, user readiness application 140 could send user readiness state 332 to separate output devices 340, including to an ADAS and/or to a separate application on a device associated with the driver (e.g., an application running on a wearable device). In such instances, both output devices 340 could respond by providing output signals 342, such as a notification signal that causes the wearable device to provide a haptic response. In some instances, an output device may directly affect the vehicle, such as when output signals 342 include one or more driving adjustment signals that adjust the direction and/or speed of the vehicle.

In various embodiments, biometric computation module 320 receives sensor data 322 from sensor(s) 120. Biometric computation module may include separate modules that analyze portions of sensor data 322 in order to provide cognitive load 324 and/or emotion metrics 326 (e.g., arousal and valence). In some embodiments, modules 314, 316 may analyze the same portions of sensor data. For example, cognitive load computation module 314 and emotion computation module 316 may separately receive image data included in sensor data 322. In such instances, cognitive load computation module 314 may analyze the image data using various pupillometry techniques and/or eye motion data to determine cognitive load 324, while emotion computation module 316 may analyze the image data to determine the facial expression, classify the facial expression as a pre-defined emotion, and acquire emotion metrics 326 corresponding to the pre-defined emotion.

User readiness computation module 330 applies various algorithms to determine an affective-cognitive load as a function of cognitive load 324 (CL) and the emotion metrics 326 that form an affective load (AL), where ACL=ƒ(CL, AL). In various embodiments, a set of ACLs may be stored in database 142. In some embodiments, user readiness computation module 330 may refer to one or more lookup tables in order to find an entry corresponding to the values for cognitive load 324 and emotion metrics 326 and may determine a corresponding ACL included in the entry. Additionally or alternatively, upon determining the ACL, user readiness computation module 330 may determine a user readiness state 332 applicable to the determined ACL. In some embodiments, the lookup table may also include an applicable action that is to be taken for the corresponding ACL. For example, a lookup table entry corresponding to a negative valence value, high arousal, and high cognitive load may indicate a high ACL and may also include commands for the ADAS to override the manual driving actions performed by the user.

In various embodiments, user readiness computation module 330 may use various algorithmic techniques to compute an ACL value from one or more of cognitive load 324 (CL) and/or emotion metrics 326, including a valence value (V), and an arousal value (A). In such instances, user readiness computation module 330 may compare the ACL value to one or more thresholds in order to determine user readiness state 332. In some embodiments, user readiness computation module 330 may select a specific algorithm to employ in order to emphasize one metric relative to other metrics. For example, user readiness computation module 330 could emphasize cognitive load 324 relative to emotion metrics 326 by applying equation 1 or equation 2 (where the offset value modifies the ACL relative to a specific threshold). In such instances, the squared value of CL causes cognitive load 324 to be the major indicator of ACL.

$$ACL = \left(\frac{1}{CL^2} \times \frac{1}{A}\right) \times V \quad (1)$$

$$ACL = \left(\frac{1}{(CL - 0.5)^2} \times \frac{1}{A}\right) \times V \quad (2)$$

In another example, user readiness computation module 330 could apply equation 3 such that the ACL is based on a combination of cognitive load 324 and the arousal value, which is modified by whether the valence value is positive or negative.

$$ACL = (CL + A) \times V \quad (3)$$

In some embodiments, user readiness computation module 330 weighs certain values in order to emphasize a specific range of values. For example, user readiness computation module 330 could apply equation 4 or 5 in order to emphasize that positive valence values are more desirable than negative valence values.

$$ACL = \left(\frac{1}{CL} + \frac{1}{A}\right) \times V \quad (4)$$

$$\frac{1}{ACL} = CL + A \times \left(\frac{1}{V+1}\right) \quad (5)$$

In some embodiments, one metric may be excluded. For example, user readiness computation module 330 could apply equation 6 such that the ACL is based on cognitive load 324 and the arousal value while ignoring the valence value.

$$\frac{1}{ACL} = CL + A \quad (6)$$

In various embodiments, user readiness computation module 330 may adjust the selected algorithm and/or equation when computing the ACL. In such instances, user readiness computation module 330 may periodically select a different algorithm and/or different equation. For example, when traffic is light, user readiness module 330 can initially select an algorithm that emphasizes cognitive load 324. When affective-cognitive load-based assistant 300 subsequently determines that traffic is heavy, user readiness computation module 330 may then select a different algorithm that weighs valence values more heavily and/or indicates that positive valence values are more desirable than negative valence values.

In some embodiments, user readiness computation module 330 may incorporate other measurements associated with the user. In some embodiments, user readiness computation module 330 may derive measures focus and engagement by simultaneously analyzing a combination of cognitive and emotional information. For example, user readiness computation module 330 could employ various statistical methods, machine-learning (ML) methods, state machines, and/or various other data structures in order to determine how results of focus and engagement (and/or other user metrics), are derived from cognitive load 324, and/or emotion metrics 326.

Additionally or alternatively, ML models may be trained from any combination of cognitive load 324, emotion metrics 326, and/or other metrics. The ML models may be trained to predict specific higher-order states of the user, such as a driver attending to a specific driving task. The ML model may then be able to generate values, such as an engagement metric, to output module 340. For example, an ADAS could receive an engagement metric, modeled from affective and cognitive signals, indicating the engagement level of a driver. In such instances, the engagement metric may be used by user readiness application 140 and/or other applications or devices to affect the control of vehicle, such that when the drivers are less engaged, certain components like (e.g., ADAS functionalities) are more proactive.

Output module 340 receives user readiness state 332, which represents the ability of the user to make a correct decision at the right time when performing a task. In certain situations, such as driving, user readiness state 332 indicates how ready the driver is to drive or act in the correct manner in a driving situation. In various embodiments, output device 340 generates output signals 342 based on user readiness state 332. For example, when user readiness state 332 indicates that the user is capable of handling a task within the environment, output signals 342 may cause one or more devices to execute tasks or provide outputs that maintain the current state of the user (e.g., maintain playback of an audio track). Conversely, when user readiness state 332 indicates that the user is not capable of handling a task within the environment, output signals 342 may cause one or more devices to execute tasks or provide outputs that assist the user in performing the requisite tasks.

In some embodiments, user readiness state 332 may indicate an expected state of the user at a future point. For example, in some embodiments, user readiness application 140 could execute various predictive techniques to determine that, based on current input values, a predicted user readiness state. In such instances, user readiness application 140 could determine whether the user will need assistance at the future point. In such instances, user readiness application 140 could generate one or more output signals 342 that modify the one or more components of the vehicle in anticipation of the user's state by the future point, thereby assisting the user in anticipation of the user's expected readiness state.

Determining User Readiness from Affective-Cognitive Load

Figure 4A:
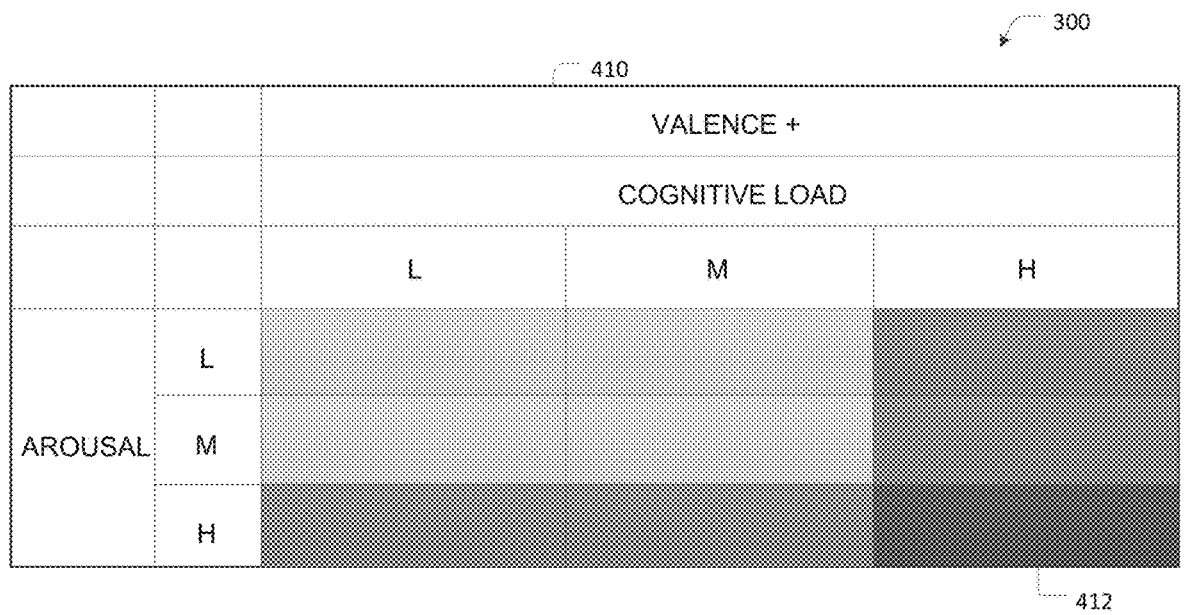
FIG. 4A illustrates an example lookup table of affective-cognitive load values associated with the user readiness application of FIG. 1, according to various embodiments.
Figure 4A:
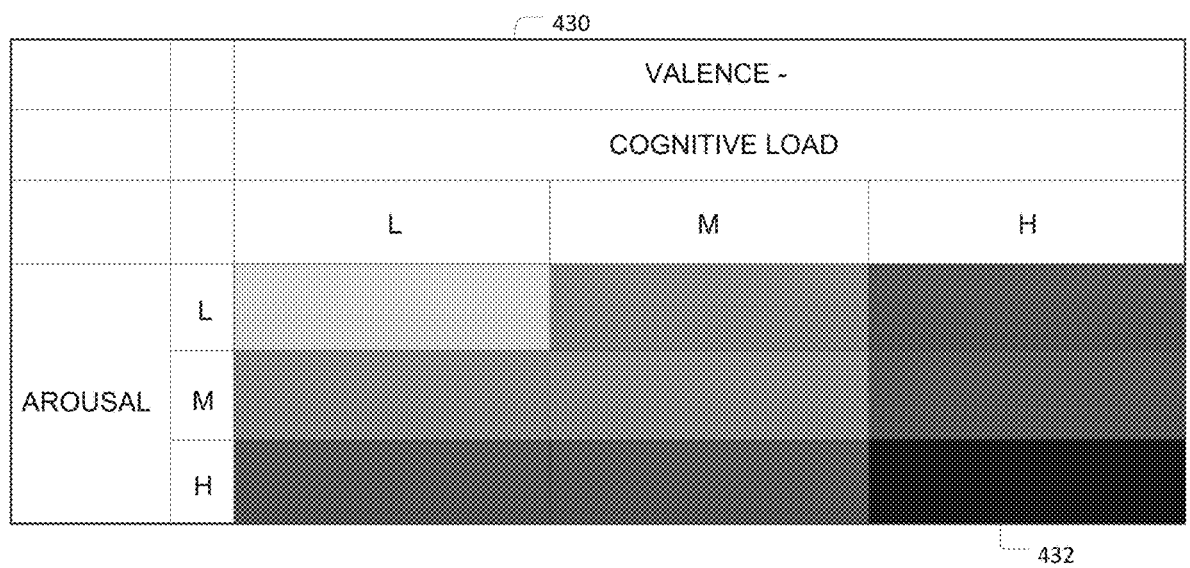
Figure 4B:
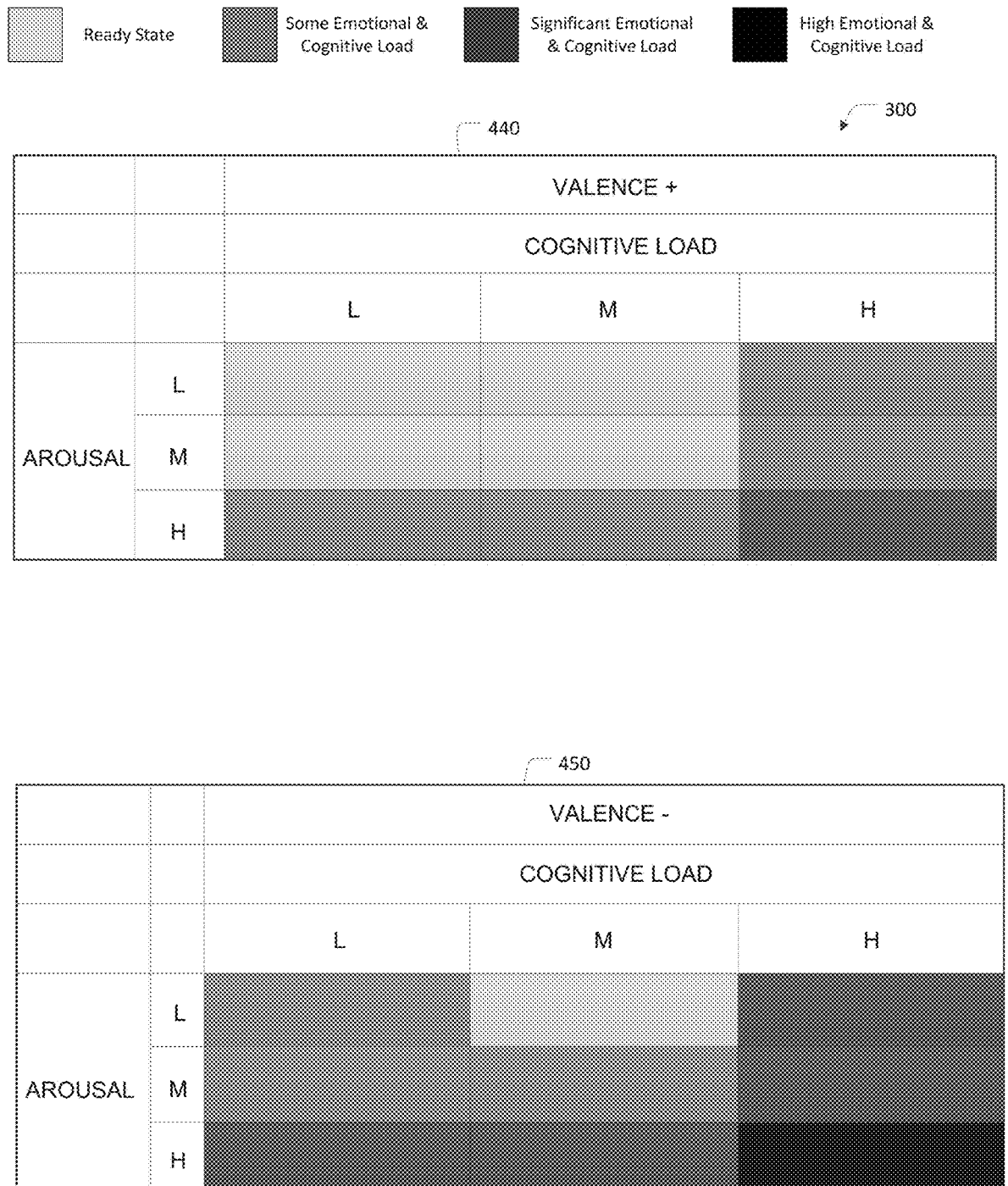
FIG. 4B illustrates another example lookup table of affective-cognitive load values associated with the user readiness application of FIG. 1, according to various embodiments.

FIG. 4A illustrates example lookup tables of affective-cognitive load values associated with the user readiness application 140 of FIG. 1, according to various embodiments. As shown, tables 400 include lookup table 410 for positive valence values and lookup table 430 for negative valence values. FIG. 4B illustrates another example lookup table of affective-cognitive load values associated with the user readiness application of FIG. 1, according to various embodiments. As shown, tables 440 include lookup table 450 for positive valence values and lookup table 460 for negative valence values. In each lookup table 400, 450, a given entry is coded as either a ready state (e.g., light grey), some emotional and cognitive load (e.g., medium grey), significant emotional and cognitive load (e.g., dark grey), and/or high emotional and cognitive load (e.g., black).

Lookup tables 400 represent conditions where the target range of the ACL is low. For example, lookup tables 400 could correspond to conditions where user performance is more effective as the ACL lowers. For example, when the ACL stems mainly from secondary tasks (e.g., texting, singing, etc.), lookup tables 440 represent conditions where the target range of the ACL is medium. For example, lookup tables 440 correspond to conditions where user performance is more effective as within a certain range. For example, when a user is engaging in too little cognitive stimulation and therefore a low ACL (e.g., bored, tired, etc.), the ACL indicates that driver readiness 332 decreases not only for high ACL, but also for low composite CL. In various embodiments, a range of high ACL values is the least desirable range and requires the most intervention by affective-cognitive load assistant 300.

In operation, user readiness computation module 330 may use cognitive load 324 and emotion metrics 326 (e.g., a specific valence value and a specific arousal value) in order to determine a specific entry in table 410 or 430. In such instances, each metric is separated into two or more discrete states. Lookup tables 410, 430 reflect certain heuristics between specific combinations of values, ACL, and user readiness state 332. For example, a combination of high cognitive load 324, a positive emotion (positive valence), and a high amount of emotion (high arousal) is less detrimental to user performance than a combination of high cognitive load 324, a negative emotion (negative valence), and a high amount of emotion. In such instances, the entry for the first combination may indicate a lower ACL and result in a user readiness state 332 within a target range (shown as entry 412), while the second combination may indicate a higher ACL and result in a user readiness state 332 outside the target range (shown as entry 432).

In some embodiments, lookup tables 410, 430 may be generated from historical data associated with a plurality of users. In such instances, database 142 the most recent lookup tables 410, 430 and may be referred to by user readiness computation module 330. In some embodiments, user readiness application 140 may adjust one or more of lookup tables 410, 430 based on one or more adjustment weights associated with a user. For example, user readiness application 140 could perform various baselining and/or ML techniques using historical ACL values and performance metrics as training data in order to apply weights to ACL determination algorithms. For example, user readiness application 140 could analyze personalized user data and determine that a particular user requires a minimum ACL and/or a negative valence value in order to perform certain driving tasks effectively. In such instances, user readiness application 140 may adjust one or more thresholds and/or one or more entries included in lookup tables 410, 430 and store the personalized adjustments in database 142.

Figure 5:
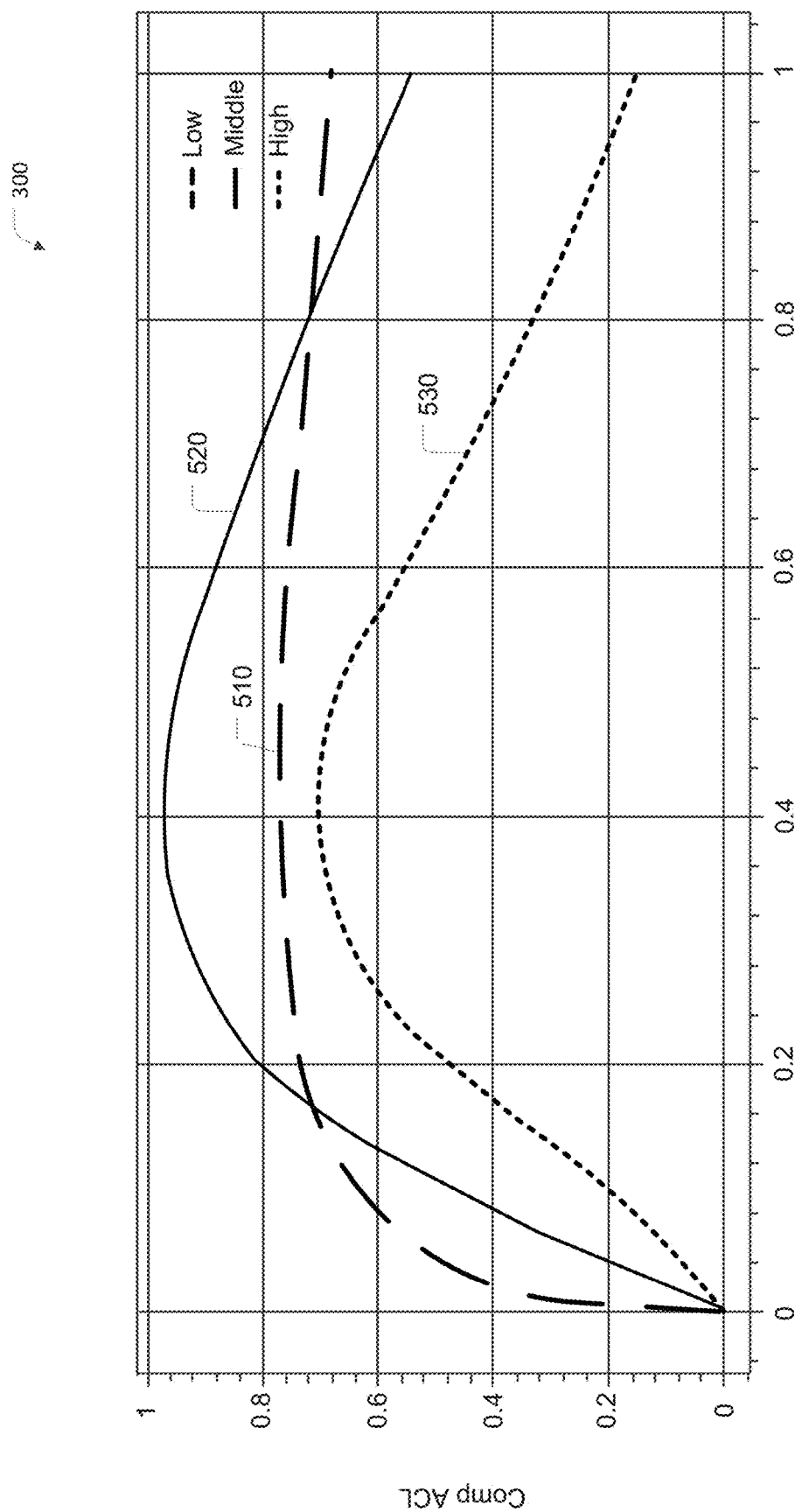
FIG. 5 illustrates an affective-cognitive load computed from various biometric values derived by the user readiness application of FIG. 1, according to various embodiments.

FIG. 5 illustrates an affective-cognitive load computed from various biometric values derived by the user readiness application 140 of FIG. 1, according to various embodiments. As shown, graph 500 illustrates ACL is a function of cognitive load 324 levels for a given arousal value.

In various embodiments, user readiness computation module 330 may apply equation 7 or 8 in order to compute ACL as a continuous function along a Weibull distribution.

$$ACL = A \times CL^A \times e^{-CL^A} \qquad (7)$$

$$ACL = CL \times A^{CL} \times e^{-A^{CL}} \qquad (8)$$

Line 510 illustrates a Weibull distribution of ACLs corresponding to a range of cognitive loads and a low arousal value. For low arousal levels, the ACL remains approximately constant for a range of cognitive loads 324 (except for very-low cognitive loads). In such instances, the ACL never rises above a certain upper limit, indicating that the driver readiness state for low arousal values never reaches the maximum value. For example, reaction times for a user could be relatively slower for low arousal values.

Line 520 illustrates a Weibull distribution of ACLs corresponding to a range of cognitive loads and a medium arousal value. For medium arousal levels, the ACL and associated user readiness state 332 may be higher for a certain range of composite loads 324. For example, above a certain cognitive load 324, the ACL for medium arousal values is higher than ACL values for lower arousal levels, indicating that the active mind of the user enables the user to handle more-demanding tasks. Once cognitive load 324 reaches an upper threshold, the cognitive ACL and user readiness state 332 begin to decrease (e.g., secondary tasks distracting the user).

Line 530 illustrates a Weibull distribution of ACLs corresponding to a range of cognitive loads and a high arousal value. When in a high emotional state, the range of best-possible performance (e.g., highest ACL values) is narrower than with lower arousal levels, as seen by lines 510, 520. Further the maximum ACL and associated user readiness state 332 are significantly lower than the maximum ACL associated with lower arousal levels.

Figure 6:
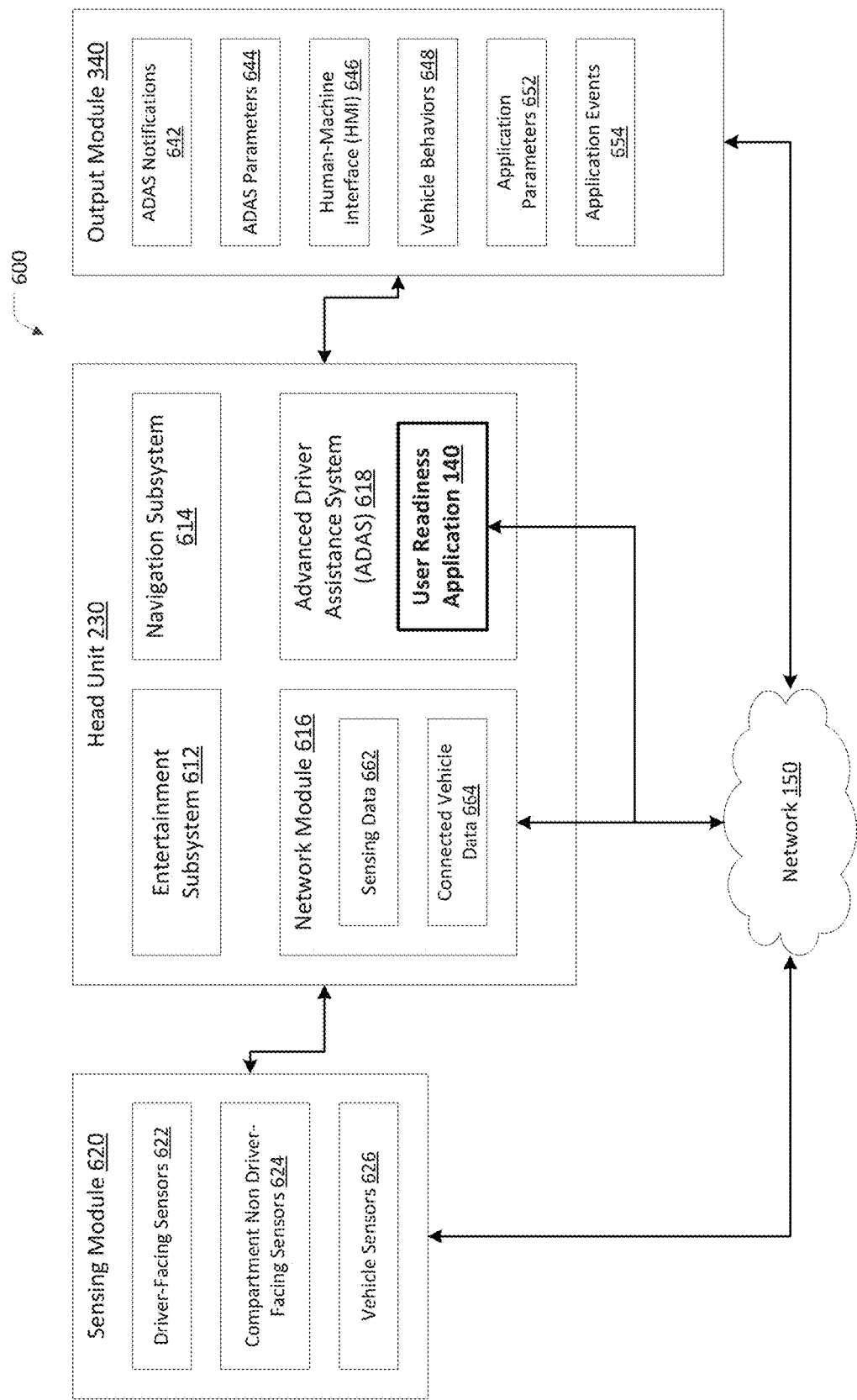
FIG. 6 illustrates an example vehicle system that includes an affective-cognitive load based digital assistant of FIG. 3, according to various embodiments.

FIG. 6 illustrates an example vehicle system 600 that includes an affective-cognitive load digital assistant 300 of FIG. 3, according to various embodiments. As shown, vehicle system 600 includes sensing module 620, head unit 230, network 150, and output module 340. Sensing module 620 includes driver-facing sensors 622 (e.g., a camera), compartment non-driver-facing sensors 624 (e.g., steering wheel sensors, pedal sensors, etc.), and vehicle sensors 626 (e.g., speedometer, accelerometer, etc.). Head unit 230 includes entertainment subsystem 612, navigation subsystem 614, network module 616, and advanced driver assistance system (ADAS) 618. Output module 340 includes ADAS notifications 642, ADAS parameters 644, human-machine interface (HMI) 646, vehicle behaviors 648, application parameters 652, and application events 654.

In various embodiments, user readiness application 140 may be included in ADAS 618 and may receive sensor data from one or more sensors 622, 624, 626 included in sensing module 620. In various embodiments, user readiness application 140 may further receive data from navigation subsystem 614 and/or network module 616. User readiness application 140 analyzes the received data to compute an ACL and determine a user readiness state 332 associated with the cognitive load and emotional state of the driver.

In various embodiments, ADAS 618 may send the user readiness state 332 to output module 340 that generates one or more output signals. In alternative embodiments, ADAS 618 may generate output signals based on the user readiness state 332. In various embodiments, the output signal may include one or more of ADAS notification 642, ADAS parameter 644, vehicle behavior 648, application parameter 652, and/or application event 654.

Sensing module 620 includes multiple types of sensors, including driver-facing sensors 622 (e.g., cameras, motion sensors, etc.), compartment non-driver facing sensors 624 (e.g., motion sensors, pressure sensors, temperature sensors, etc.), and vehicle sensors (e.g., outward-facing cameras, accelerometers, etc.). In various embodiments, sensing module 620 provides a combination of sensor data that describes the context in which combined affective-cognitive load are being observed in more detail. For example, sensing module 620 could provide a set of values associated with the operation of the vehicle (e.g., angular velocity of rear tires, velocity of the pedal movement, velocity of the vehicle, etc.). In such instances, user readiness application 140 could determine a cognitive load value and/or an emotional load value based on the received values, such as by comparing the measured velocity of the vehicle compared to the speed limit of the location, and/or the velocity of surrounding vehicles.

In various embodiments, vehicle sensors 626 may further include other external sensors. Such external sensors may include optical sensors, acoustic sensors, road vibration sensors, temperature sensors, etc. In some embodiments, sensing module and/or network module 616 may acquire other external data, such as geolocation data (e.g., GNNS systems, including a global positioning system (GPS), Glonass, Galileo, etc.). In some embodiments, navigation data and/or geolocation data may be combined to predict changes to the ACL based on expected driving conditions. For example, an expected traffic jam may cause user readiness application 140 to predict an increase in the ACL upon the vehicle reaching affected area.

Network module 616 translates results of sensor module 620. In various embodiments, network module 616 may retrieve specific values, such as sensing data 662, connected vehicle data 664, and/or historical data (e.g., previous ACLs, calculations that were computed by remote devices, etc.). For example, user readiness computation module 330 could compare the current ACL with previous performances before mapping the ACL to a driver readiness value. In some embodiments, the driver readiness 332 may include a notification indicating whether the driver has improved, remained more focused, engaged, etc., compared to past performances.

In some embodiments, network module 616 may transmit data acquired by head unit, such as one or more ACLs, user readiness state 332, and/or sensing data 662 acquired by sensor module 620. In such instances, one or more devices connected to network 150 may merge data received from network module 616 with data from other vehicles, and/or infrastructure before being consumed by computation modules. For example, one or more devices may accumulate and compile sensing data in order to associate driving conditions with required driver readiness.

For example, one or more devices could accumulate multiple ACL computations into an aggregate measure of the focus or engagement of a group. For example, a smart home system that includes affective-cognitive load based assistant 300 may compute ACLs for each member in a room and may generate an aggregate user readiness state corresponding to the multiple members in the rooms before determining the brightness of lighting of a given room. In another example, affective-cognitive load-based assistant 300 could emphasize certain members (e.g., emphasize the ACLs of a group of guests).

Output module 340 performs one or more actions in response to a user readiness state 332 provided by ADAS 618. For example, output module 340 may generate one or more output signals 341 in response to user readiness state 332 that modifies an application and/or interface. For example, output module 340 could generate one or more output signals 341 to modify HMI 646 to display notification messages and/or alerts. In another example, output module 340 could generate one or more output signals to modify an application. In such instances, the output signal 341 may include application parameters 652 and/or application events 654.

In various embodiments, ADAS notifications 642 may include light indications, such as ambient lights and mood lights, audio notifications, voice notifications (e.g., a voice assistant), visual notification messages, haptic notifications in the vehicle (e.g., steering wheel, seat, head rest, etc.) or wearable device or touchless haptic notifications, etc.

In various embodiments, ADAS parameters 644 may include various operating parameters, settings, or actions. For example, ADAS parameters 644 could include vehicle climate control settings (e.g., window controls, passenger compartment temperature, increasing fan speed, etc.), and/or olfactory parameters, such as emitting specific fragrances that are calming or stimulating. In various embodiments, ADAS parameters 644 may include emergency calling parameters, such as triggering the dialing of one or more emergency phone numbers or suggesting that the user connect to a specific contact situations that may require immediate assistance and/or response.

In various embodiments, ADAS parameters 644 may dynamically activate L2+/L3+ capabilities, such as lane assist, collision avoidance, and/or autonomous driving. In some embodiments, ADAS parameter 644 may be a binary activation signal (on/off); alternatively, ADAS parameters 644 may be activation signal that provides a more-gradual activation (e.g., with varying degrees of automated correction when the driver seems to deviate from their lane). In some embodiments, ADAS parameters 644 may dynamically activate the collision avoidance systems. For example, output module 340 may dynamically generate ADAS parameters 644 that adapt the parameters of the system (e.g., warning time, brake intensity, etc.) depending on user readiness state 332.

In some embodiments, other systems may generate responses based on user readiness state 332. For example, navigation subsystem 614 could generate specific route suggestions based on the user readiness state, such as avoiding routes that require significant focus or attention.

Additionally or alternatively, entertainment subsystem 612 may play specific tracks associated with specific moods in order to maintain user readiness state 332, or to alter user readiness state 332.

Figure 7:
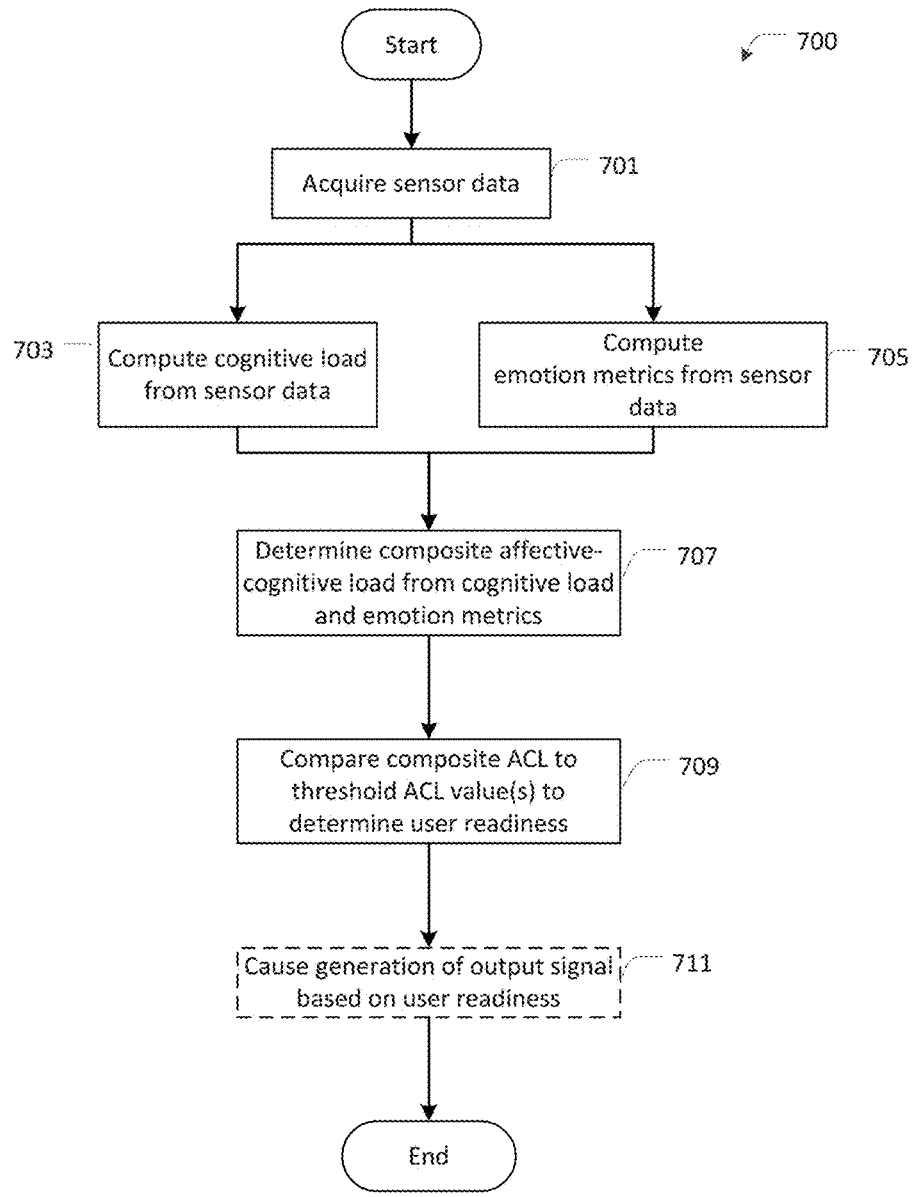
FIG. 7 is a flow diagram of method steps for generating an output signal based on an affective-cognitive load, according to various embodiments.

FIG. 7 is a flow diagram of method steps for generating an output signal based on an affective-cognitive load, according to various embodiments. Although the method steps are described with respect to the systems of FIGS. 1-6, persons skilled in the art will understand that any system configured to perform the method steps, in any order, falls within the scope of the various embodiments.

As shown, method 700 begins at step 701, where user readiness application 140 acquires sensor data. In various embodiments, various sensor(s) 120 acquire sensor data related to the brain activity and/or emotional state of a user. For example, sensor 120 may include a camera that acquires sensor data focused on the face of the user.

At step 703, user readiness application 140 computes a cognitive load from the sensor data. In various embodiments, user readiness application 140 may analyze portions of the acquired sensor data in order to estimate the cognitive load currently being experienced by a user. For example, user readiness application 140 may perform various pupillometry techniques on received image data in order to determine fluctuations in the pupil of the user. User readiness application 140 may then compute the cognitive load from the pupil data. Additionally, or alternatively, user readiness application 140 may perform various eye motion analyses on received image data in order to determine eye saccades, eye fixations, and the like, from the eyes of the user. User readiness application 140 may then compute the cognitive load from the eye saccades, eye fixations, and the like.

At step 705, user readiness application 140 computes one or more emotion metrics from the sensor data. In various embodiments, it may analyze portions of the acquired sensor data in order to estimate emotion parameterized metrics currently being experienced by a user. For example, user readiness application 140 may perform various facial expression estimation techniques on received image data in order to determine the emotion being experienced by the user. In another example, additionally or alternatively to facial expression estimation, user readiness application 140 may perform various voice tone analyses on received audio data in order to determine the emotion being experienced by the user. User readiness application 140 may map the estimated emotion to specific arousal and valence values.

At step 707, user readiness application 140 determines an affective-cognitive load (ACL) as a composite of the cognitive load and emotion metrics. In various embodiments, user readiness application 140 may execute one or more algorithmic techniques in order to compute an affective-cognitive load (ACL) of the user. For example, user readiness application 140 may compute the ACL as a function of the inverses of the cognitive load and the arousal, multiplied by the valence (e.g., equation 4). Such an algorithm emphasizes positive emotional valence values for a given set of cognitive load and arousal values. In another example, user readiness application 140 could refer to one or more lookup tables to find an entry that specifies a specific ACL for a specific combination of cognitive load, arousal, and valence.

At step 709, user readiness application 140 compares the ACL to one or more threshold ACL values in order to determine a user readiness state. In various embodiments, user readiness application 140 may compare the ACL value to one or more thresholds that separate user readiness states. For example, user readiness application 140 may compare ACL to a minimum threshold and a maximum threshold in order to determine that ACL is within a target ACL threshold range associated with a particular user readiness state. In such instances, user readiness application 140 may determine that heuristics indicate that the target ACL range corresponds to a medium level of user readiness, indicating that the user is engaged enough to respond to stimuli without being overwhelmed. In other embodiments, the minimum threshold separate a medium ACL range from a lower ACL range that corresponds to the target ACL range. In such instances, a medium ACL value could correspond to a user readiness state outside the target range, indicating that some assistance to the user may be necessary to perform the required tasks.

At step 711, user readiness application 140 may optionally cause output device 340 to generate an output signal based on the user readiness state. In various embodiments, user readiness application 140 may send to output module 340 the user readiness state. In such instances, receiving the user readiness state causes output module 340 to generate one or more output signals. In various embodiments, the output signal may cause one or more devices, such as an assisted driving system, display device, and/or feedback system, to adjust one or more parameters associated with handling a task. For example, upon receiving a user readiness state indicating that intervention is required, output device 340 could generate one or more output signals to assist the user in handling a task and/or lowering the ACL such that the user will soon be able to successfully handle the task.

In sum, an affective-cognitive based load digital assistant receives sensor data and determines the readiness of a user to handle a task within an environment. Various sensors acquire sensor data associated with the user or the environment and sends the sensor data to a user readiness application included in the affective-cognitive load based digital assistant. The user readiness application computes from the sensor data various biometric values associated with the psychophysiological state of a user. Such biometric values include a cognitive load that estimates the amount of brain activity that a user is employing, and an affective load that estimates an emotional load that a user is experiencing. In various embodiments, the affective load may include one or more separate emotional metrics, such as separate arousal and/or valence values. Upon determining separate biometric values for a user, the user readiness application analyzes the cognitive load and affective load using one or more algorithmic techniques to determine an affective-cognitive load (ACL), which indicates the user's overall mental activity. The user readiness application then determines a user readiness state, which indicates the ability of the user to manage a set of tasks. The user readiness state determined by the user readiness application causes output devices and/or other applications to assist the user at a degree that corresponds to the determined user readiness state.

At least one technological advantage of the affective-cognitive load based digital assistant is that computing a user readiness state as a composite of direct measurements that estimate the cognitive load and the emotional state of the user provides a more accurate indication of the ability of the user to handle tasks. In particular, by combining emotion recognition and cognitive load, the affective-cognitive load based digital assistant can describe both the quality of the cognition (the operations being done by the mind, measured as cognitive load), as well as the emotion. Further, the mental state estimated by the affective-cognitive load digital assistant is associated with autonomic body systems making the estimations less susceptible to error. As a result, systems that assist the user in conducting certain tasks can more accurately assist the user based on the estimated brain activity and emotional state of the user.

1. In various embodiments, a computer-implemented method comprises receiving, from at least one sensor, sensor data associated with an environment, computing, based on the sensor data, a cognitive load associated with a user within the environment, computing, based on the sensor data, an affective load associated with an emotional state of the user, determining, based on both the cognitive load at the affective load, an affective-cognitive load, determining, based on the affective-cognitive load, a user readiness state associated with the user, and causing one or more actions to occur based on the user readiness state.

2. The computer-implemented method of clause 1, where the affective load comprises an arousal value and a valence value, and determining the affective-cognitive load comprises searching, based on the cognitive load, the arousal value, and the valence value, one or more lookup tables that include entries specifying affective-cognitive loads, and identifying an entry included in the one or more lookup tables, wherein the entry corresponds to a set of the cognitive load, the arousal value, and the valence value.

3. The computer-implemented method of clause 1 or 2, where the sensor data comprises image data.

4. The computer-implemented method of any of clauses 1-3, where the affective load comprises an arousal value and a valence value, and determining the affective-cognitive load comprises applying an algorithmic technique to compute the affective-cognitive load as a function of the cognitive load and at least one of the arousal value or the valence value.

5. The computer-implemented method of any of clauses 1-4, where the algorithmic technique includes applying a Weibull distribution function based on the cognitive load and the arousal value.

6. The computer-implemented method of any of clauses 1-5, where computing the cognitive load comprises determining one or more eye parameters from image data included in the sensor data, and computing the cognitive load from the one or more eye parameters, and computing the affective load comprises determining a pre-defined emotion from the sensor data, and identifying an arousal value corresponding to the pre-defined emotion, and identifying a valence value corresponding to the pre-defined emotion, where the arousal value and the valence value are included in the affective load.

7. The computer-implemented method of any of clauses 1-6, where causing the one or more actions to occur based on the user readiness state comprises causing an output device to generate an output signal based on the user readiness state.

8. The computer-implemented method of any of clauses 1-7, where the output signal causes the output device to change at least one operating parameter.

9. The computer-implemented method of any of clauses 1-8, where the output signal causes at least one notification message to be emitted from the output device.

10. The computer-implemented method of any of clauses 1-9, where the output signal causes one or more lights to change brightness.

11. In various embodiments, one or more non-transitory computer-readable media store instructions that, when executed by one or more processors, cause the one or more processors to perform the steps of receiving, from at least one sensor, sensor data associated with an environment, computing, based on the sensor data, a cognitive load associated with a user within the environment, computing, based on the sensor data, an affective load associated with an emotional state of the user, applying an algorithmic technique to compute an affective-cognitive load as a function of the cognitive load and the affective load, determining, based on the affective-cognitive load, a user readiness state associated with the user, and causing one or more actions to occur based on the user readiness state.

12. The one or more non-transitory computer-readable media of clause 11, wherein the sensor data comprises image data.

13. The one or more non-transitory computer-readable media of clause 11 or 12, where computing the cognitive load comprises determining one or more eye parameters from image data included in the sensor data, and computing the cognitive load from the one or more eye parameters, and computing the affective load comprises determining a pre-defined emotion from the sensor data, and identifying an arousal value corresponding to the pre-defined emotion, and identifying a valence value corresponding to the pre-defined emotion, where the arousal value and the valence value are included in the affective load.

14. The one or more non-transitory computer-readable media of any of clauses 11-13, where the sensor data comprises biometric data including at least one of a pupil size, a heart rate, a galvanic skin response, or a blood oxygenation level.

15. The one or more non-transitory computer-readable media of any of clauses 11-14, further including instructions that, when executed by the one or more processors, cause the one or more processors to perform the steps of computing, based on the sensor data, a second cognitive load associated with a second user within the environment, computing, based on the sensor data, a second affective load associated with a second emotional state of the second user, determining, based on both the second cognitive load at the affective load, a second affective-cognitive load, combining the affective-cognitive load and the second affective-cognitive load to generate an aggregate affective-cognitive load, determining, based on the aggregate affective-cognitive load, an aggregate user readiness state associated with both the user and the second user, and causing one or more actions to occur based on the aggregate user readiness state.

16. In various embodiments, an affective-cognitive load based device comprises at least one sensor configured to acquire sensor data, a memory storing a user readiness application, and a processor that is coupled at least to the memory and, when executing the user readiness application, is configured to receive, from the at least one sensor, sensor data associated with an environment, compute, based on the sensor data, a cognitive load associated with a user within the environment, compute, based on the sensor data, at least one of an arousal value or a valence value associated with an emotional state of the user, determine, based on the cognitive load and at least one of the arousal value or the valence value, an affective-cognitive load, determine, based on the affective-cognitive load, a user readiness state associated with the user, and cause one or more actions to occur based on the user readiness state.

17. The affective-cognitive load-based device of clause 16, where the sensor data comprises image data.

18. The affective-cognitive load-based device of clause 16 or 17, where determining the affective-cognitive load comprises applying an algorithmic technique to compute the affective-cognitive load as a function of the cognitive load and at least one of the arousal value or the valence value.

19. The affective-cognitive load-based device of any of clauses 16-18, where the affective-cognitive load-based device is included in an advanced driver assistance system (ADAS) of a vehicle.

20. The affective-cognitive load-based device of any of clauses 16-19, wherein the processor configured to cause one or more actions to occur comprises generating an output signal that causes the ADAS to change at least one ADAS parameter.

Any and all combinations of any of the claim elements recited in any of the claims and/or any elements described in this application, in any fashion, fall within the contemplated scope of the present invention and protection.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "module," a "system," or a "computer." In addition, any hardware and/or software technique, process, function, component, engine, module, or system described in the present disclosure may be implemented as a circuit or set of circuits. Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

Aspects of the present disclosure are described above with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general-purpose computer, special purpose computer, or other programmable data processing apparatus to produce a machine. The instructions, when executed via the processor of the computer or other programmable data processing apparatus, enable the implementation of the functions/acts specified in the flowchart and/or block diagram block or blocks. Such processors may be, without limitation, general purpose processors, special-purpose processors, application-specific processors, or field-programmable gate arrays.

The flowchart and block diagrams in the figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

While the preceding is directed to embodiments of the present disclosure, other and further embodiments of the disclosure may be devised without departing from the basic scope thereof, and the scope thereof is determined by the claims that follow.

What is claimed is:

1. A computer-implemented method comprising:
   receiving, from at least one sensor, sensor data associated with an environment;
   computing, based on the sensor data, a cognitive load value associated with a user within the environment;
   computing, based on the sensor data, an arousal value and a valence value associated with an emotional state of the user;
   multiplying the valence value by a combination of the cognitive load value and the arousal value to generate an affective-cognitive load;
   comparing the affective-cognitive load with one or more thresholds to determine a user readiness state associated with the user; and
   modifying a vehicle operation to assist the user in performing a driving action to a degree that corresponds to the user readiness state.

2. The computer-implemented method of claim 1, wherein the sensor data comprises image data.

3. The computer-implemented method of claim 1, further comprising weighting at least one of the cognitive load, the arousal value, or the valence value.

4. The computer-implemented method of claim 1, wherein:
   the step of computing the cognitive load comprises:
      determining one or more eye parameters from image data included in the sensor data, and
      computing the cognitive load from the one or more eye parameters; and
   the step of computing the arousal value and the valence value comprises:
      determining a pre-defined emotion from the sensor data, and identifying the arousal value corresponding to the pre-defined emotion, and identifying the valence value corresponding to the pre-defined emotion.

5. The computer-implemented method of claim 1, wherein the step of modifying the vehicle operation to assist the user in performing the driving action to the degree that corresponds to the user readiness state comprises causing an advanced driver assistance system (ADAS) to generate an operating parameter to dynamically activate the vehicle operation.

6. The computer-implemented method of claim 1, further comprising causing, based on the user readiness state, at least one notification message to be emitted from an output device.

7. The computer-implemented method of claim 1, further comprising causing, based on the user readiness state, one or more lights to change brightness.

8. The computer-implemented method of claim 1, wherein the step of modifying the vehicle operation causes the affective-cognitive load to transition into a target affective-cognitive load threshold range.

9. The computer-implemented method of claim 1, wherein the step of comparing the affective-cognitive load to the one or more thresholds comprises comparing the affective-cognitive load to a minimum threshold and a maximum threshold defining a target affective-cognitive load threshold range.

10. One or more non-transitory computer-readable media storing instructions that, when executed by one or more processors, cause the one or more processors to perform the steps of:

receiving, from at least one sensor, sensor data associated with an environment;

computing, based on the sensor data, a cognitive load value associated with a user within the environment;

computing, based on the sensor data, an arousal value and a valence value associated with an emotional state of the user;

multiplying the valence value by a combination of the cognitive load value and the arousal value to generate an affective-cognitive load;

comparing the affective-cognitive load with one or more thresholds to determine a user readiness state associated with the user; and modifying a vehicle operation to assist the user in performing a driving action to a degree that corresponds to the user readiness state.

11. The one or more non-transitory computer-readable media of claim 10, wherein the sensor data comprises image data.

12. The one or more non-transitory computer-readable media of claim 10, wherein:

the step of computing the cognitive load comprises:
determining one or more eye parameters from image data included in the sensor data, and
computing the cognitive load from the one or more eye parameters; and the step of computing the arousal value and the valence value comprises:
determining a pre-defined emotion from the sensor data, and
identifying the arousal value corresponding to the pre-defined emotion, and
identifying the valence value corresponding to the pre-defined emotion.

13. The one or more non-transitory computer-readable media of claim 10, wherein the sensor data comprises biometric data including at least one of a pupil size, a heart rate, a galvanic skin response, or a blood oxygenation level.

14. The one or more non-transitory computer-readable media of claim 10, further including instructions that, when executed by the one or more processors, cause the one or more processors to perform the steps of:

computing, based on the sensor data, a second cognitive load associated with a second user within the environment;

computing, based on the sensor data, a second valence value and a second arousal value associated with a second emotional state of the second user;

combining the second cognitive load, the second valence value, and the second arousal value to generate a second affective-cognitive load;

combining the affective-cognitive load and the second affective-cognitive load to generate an aggregate affective-cognitive load;

comparing the aggregate affective-cognitive load with the one or more thresholds to determine an aggregate user readiness state associated with both the user and the second user; and causing one or more actions to occur based on the aggregate user readiness state.

15. An affective-cognitive load-based device, comprising:
at least one sensor configured to acquire sensor data;
a memory storing a user readiness application; and
a processor that is coupled at least to the memory and, when executing the user readiness application, is configured to:

receive, from the at least one sensor, sensor data associated with an environment;

compute, based on the sensor data, a cognitive load value associated with a user within the environment;

compute, based on the sensor data, an arousal value and a valence value associated with an emotional state of the user;

multiply the valence value by a combination of the cognitive load value and the arousal value to generate an affective-cognitive load;

compare the affective-cognitive load with one or more thresholds to determine a user readiness state associated with the user; and modify a vehicle operation to assist the user in performing a driving action that corresponds to the user readiness state.

16. The affective-cognitive load-based device of claim 15, wherein the sensor data comprises image data.

17. The affective-cognitive load-based device of claim 15, wherein, when executing the user readiness application, the processor is further configured to weight at least one of the cognitive load, the arousal value, or the valence value.

18. The affective-cognitive load-based device of claim 15, wherein the affective-cognitive load-based device is included in an advanced driver assistance system (ADAS) of a vehicle.

19. The affective-cognitive load-based device of claim 18, wherein the processor configured to modify the vehicle operation comprises causing the ADAS to generate at least one ADAS parameter to dynamically activate the vehicle operation.

* * * * *